United States Patent [19]
Rix
[11] Patent Number: 4,796,609
[45] Date of Patent: Jan. 10, 1989

[54] TILTABLE BACK TRACTION TABLE HAVING ADJUSTABLE BALANCE POINT AND BUMPER

[76] Inventor: Emmet T. Rix, P.O. Box 261, Paradise, Calif. 95967

[21] Appl. No.: 36,885
[22] Filed: Apr. 10, 1987
[51] Int. Cl.[4] ........ A61F 5/00
[52] U.S. Cl. ........ 128/74; 128/70
[58] Field of Search ........ 128/24 R, 68 R, 69, 128/70, 71, 74, 75, 72, 73

[56] References Cited

U.S. PATENT DOCUMENTS

| | | | |
|---|---|---|---|
| 1,693,810 | 12/1928 | Daniels et al. | 128/70 |
| 2,983,930 | 5/1961 | Porriff | 128/70 |
| 3,081,085 | 3/1963 | De Girolamo | 128/70 |
| 3,286,708 | 11/1966 | Gärtner | 128/70 |
| 3,351,051 | 11/1967 | Jennings | 128/24 R |
| 3,570,479 | 3/1971 | Horn | 128/71 |
| 3,752,153 | 8/1973 | Copeland | 128/70 |
| 3,794,023 | 2/1974 | Bradley | 128/24 R |
| 4,214,790 | 7/1980 | Sieber | 128/70 |
| 4,419,989 | 12/1983 | Herbold | 128/74 |
| 4,534,554 | 8/1985 | Miller | 128/75 |
| 4,739,749 | 4/1988 | Lindley | 128/75 |

FOREIGN PATENT DOCUMENTS

| | | | |
|---|---|---|---|
| 2808077 | 9/1978 | Fed. Rep. of Germany | 128/70 |
| 854 | of 1893 | United Kingdom | 128/70 |

*Primary Examiner*—Edgar S. Burr
*Assistant Examiner*—Tonya Lamb
*Attorney, Agent, or Firm*—Leonard D. Schappert

[57] ABSTRACT

A back traction table is provided having a tiltable platform positioned on a base and including offset retainers whereby the balance point of the tiltable platform can be changed, further including a leg support which captures an individual's leg so that the individual does not slide during use of the back traction table.

5 Claims, 2 Drawing Sheets

TILTABLE BACK TRACTION TABLE HAVING ADJUSTABLE BALANCE POINT AND BUMPER

BACKGROUND OF THE INVENTION

1. Field of the Invention

The present invention relates generally to devices for use in reducing and/or correcting stresses related to back problems, and more specifically to devices designed to invert an individual to some degree so that the forces of gravity are reversed for the period of time during which the individual is inverted. It is well established that placing the normal individual in a recumbent position with the head downward for a limited period of time aids in reducing stresses relating to back problems and results in beneficial and healthful effects. Such stresses can be attributed to the fact that, as a result of mankind's vertical posture, the pull of gravity creates stresses on the nerves and blood vessels, potentially pinching nerves in the spinal column. It is toward the reduction of the deteriorative effects of such vertical posture and gravitational forces that the present invention is directed.

2. Description of the Prior Art

Past inventions directed toward relieving back stresses and minimizing the effect of gravity on the posture of mankind have been directed toward tiltable reclining boards and seats for improving back posture, some of such devices tilting backward to a specific angle, others providing the possibility of substantially inverting an individual so that his feet are directly above his head. Such inventions have included back posture boards, full-body weight traction devices, tiltable reclining and seating devices, head stand exercises and other traction devices directed toward relieving back and other stresses. In each case, the device to be utilized has been either costly, complex or difficult for a physically limited individual to operate without help from others. As is shown by the objects and descriptions which follow, the present invention is designed to enable physically limited individuals to gain relief as desired without dependence upon other persons.

SUMMARY OF THE INVENTION

The present invention provides a back traction table which includes adjustment means designed so that users of any size and/or with physical limitations can achieve a somewhat inverted posture easily while maintaining sufficient control so that they can easily return to a horizontal position. The present invention further includes features designed to guarantee stability of the back traction table, in addition to features designed to ensure that a user of the back traction table is held in a stationary position while utilizing the back traction table.

One of the objects of the present invention is to provide a back traction table which allows an individual to recline in a recumbent position with the lower part of his body angled upward and his head angled downward to achieve healthful therapeutic effects.

Another object of the present invention is to provide a back traction table which is balanced and which provides means for easily shifting its fulcrum in order to facilitate use by individuals of different body types and structures.

A further object of the present invention is to provide a back traction table which, because of the balance achievable by the shifting of its fulcrum, is usable by individuals having limited physical ability without the aid of other individuals.

Another object of the present invention is to provide a back traction table which provides means for keeping an individual from sliding on the back traction table while he is lying in a recumbent, head-downward position.

A further object of the present invention is to provide a back traction table which, in an alternative embodiment, provides means for utilizing a chain hoist to position an individual on the table in a reclining, head-downward position.

The foregoing objects, as well as other objects and benefits of the present invention, are made more apparent by the descriptions and claims which follow.

DESCRIPTION OF THE PREFERRED EMBODIMENT

The present invention consists of a back traction table 10 which includes a platform 11 which is balanced to facilitate use by individuals desiring to recline in a head-down position. It further includes means for holding the individual utilizing the back traction table 10 laterally during such use. It also includes balancing means consisting of a rod 35 and retainers 34 for changing the center of gravity of the platform 11 of the back traction table 10 to allow use by individuals of different body types and structures.

Figure 1:
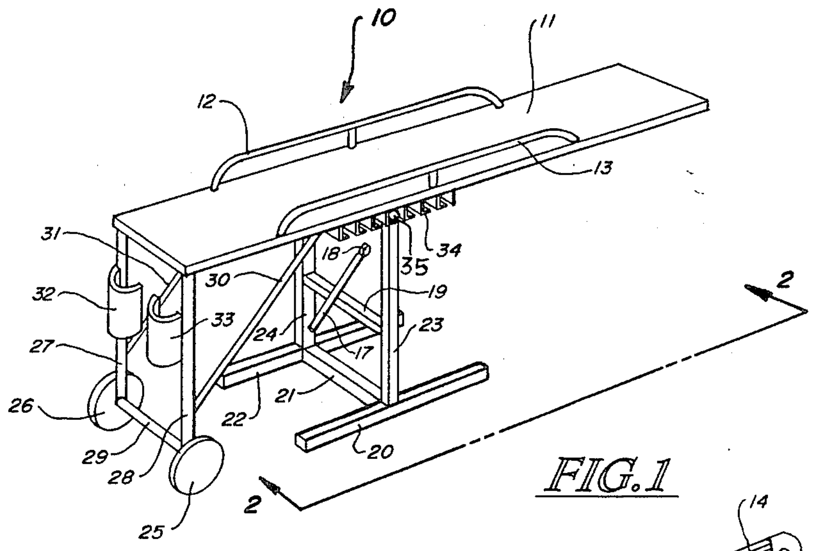
FIG. 1 is a perspective view showing the construction of the back traction table.

FIG. 1 of the drawings is a perspective view of back traction table 10 illustrating the structure employed in accomplishing the foregoing objects. More specifically, a platform 11 is provided upon which an individual may lie in order to relieve back stresses. Side rails 12 and 13 are provided to minimize the possibility of an individual's rolling or falling off the side of platform 11, but also for use as hand grips to assist an individual in positioning himself properly on platform 11 in order to achieve the proper center of gravity for shifting the angle of the platform 11 to position the individual utilizing back traction table 10 in a head-down position. Side rails 12 and 13 are attached to platform 11 by welding or any other acceptable fastening means. The base upon which platform 11 is balanced consists of legs 23 and 24, which are vertically stabilized by rigid attachment to rods 19 and 35 and to supports 20, 21 and 22. Specifically, platform 11 balances on rod 35, which is also attached to legs 23 and 24. A spring-loaded bumper 17 with a roller 18 positioned on the end thereof is attached to rod 19 by welding or other appropriate attaching means and oriented so that, as the angle of the platform 11 is changed as shown by arrows A of FIG. 2, the bottom of platform 11 contacts roller 18 of bumper 17, limiting the movement of platform 11 and cushioning it. A support structure consisting of legs 27 and 28, which are rigidly attached to platform 11, and an axle 29 attached to legs 27 and 28 with wheels 25 and 26 positioned thereon is provided to hold an individual user's legs in position during use of the back traction table 10. Platform 11 can be lifted at the end opposite legs 27 and 28 and wheeled to any desired location. Supports 30 and 31, which extend between leg 28 and platform 11 and between leg 27 and platform 11 respectively, are provided to ensure the structural integrity of back traction table 10. Leg supports 32 and 33, which consist of semi-cylindrical pieces of material such as PVC or any other acceptable material rigidly attached to legs 27 and 28 respectively, are provided so that an individual sitting on top of platform 11 can, by positioning his legs inside leg supports 32 and 33, ensure that his body will not slide on platform 11 when its angle is shifted to position him head-down.

Figure 2A:
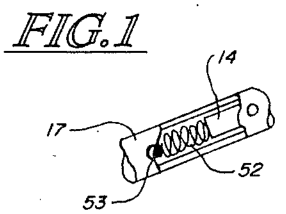
FIG. 2A is an expanded cutaway view of the encircled area of FIG. 2 referred to as 2A.
Figure 2:
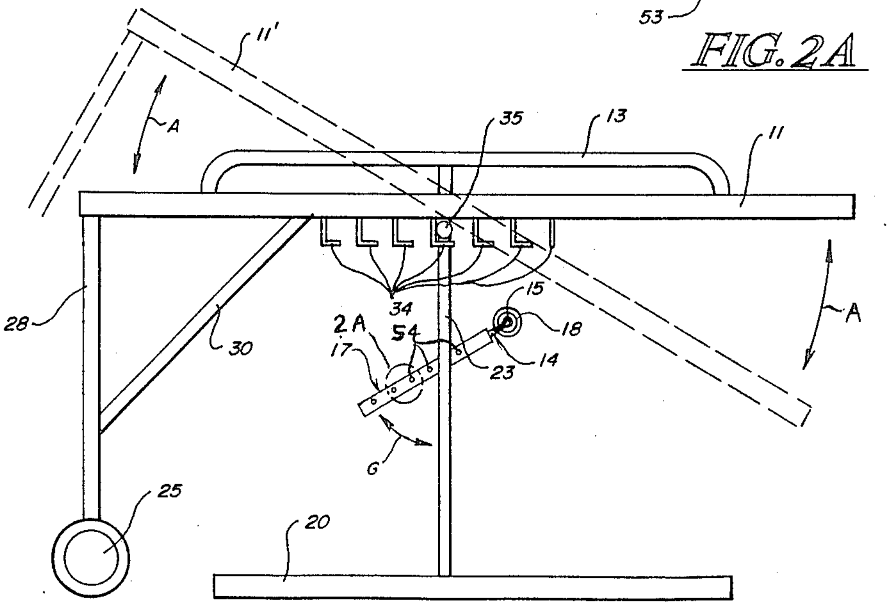
FIG. 2 is a side view of the back traction table of FIG. 1 taken along lines 2—2 of FIG. 1 and showing movements involved in reclining the back traction table.

FIG. 2 of the drawings is a side view of back traction table 10 taken along lines 2—2 of FIG. 1. The movement involved in tilting back traction table 10 is here shown by arrows A and dashed lines. Specifically, platform 11 is positioned and balanced on rod 35, which is attached to legs 23 and 24. The user positions platform 11 on rod 35 by moving rod 35 into one of the retainers 34. Shifting the position of platform 11 to position rod 35 in a different retainer changes the fulcrum point, thus shifting the center of gravity of platform 11. As a result of this adjustability, back traction table 10 adapts for use by individuals having bodies with different structures and weight distribution. A bumper 17 is provided to limit movement of platform 11 along arrows A. The angle G of bumper 17 is set to minimize stress of the attachment of bumper 17 to rod 19. Bumper 17 has multiple holes 54 through which a pin fits to adjust the lateral position of roller 18. Bumper 17 consists of a hollow rod as shown in FIG. 2A into which rod 14 and spring 52 are positioned. Roller 18 is attached at axle 15 to rod 14. The user of back traction table 10 adjusts the lateral position of rod 14 and roller 18 by positioning pin 53 in various holes 54. When the bottom surface of platform 11 contacts roller 18, spring 52 compresses against pin 53, minimizing the jarring effect to the user. Bumper 17, when extended out, limits movement as shown by platform 11' in dashed lines. When positioned as shown in solid lines, it will enable the platform 11 to move into a substantially vertical position.

Figure 3:
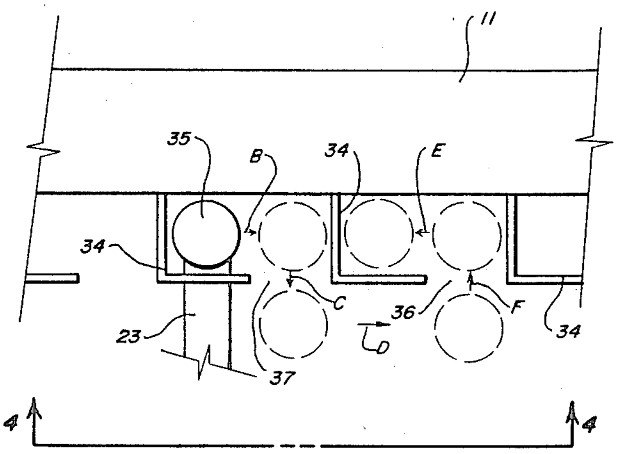
FIG. 3 is an expanded side view of the center portion of the platform utilized with the back traction table showing how the fulcrum of the platform of the back traction table can be shifted in order to shift the center of gravity.

FIG. 3 is an expanded side view showing the means for adjusting the center of gravity of platform 11. More specifically, platform 11 is shown balanced on rod 35 with rod 35 positioned inside one of retainers 34. The gaps 36 and 37 between retainers 34 are made just large enough to allow rod 35 to pass therethrough, thereby virtually eliminating the possibility that platform 11 will separate from rod 35 during use. FIG. 3 further shows the operation involved in changing the position of platform 11 to shift the point at which it balances on rod 35. More specifically, rod 35 is moved as shown by dashed lines to the right as shown by arrow B, through opening 37 as shown by arrow C, to the right as shown by arrow D to a position below and in line with opening 36, up through opening 36 as shown by arrow F, and to the left as shown by arrow E. Retainers 34 are constructed of angle iron or any other structural material formed to capture rod 35 as shown, and are attached to platform 11 by welding or any other acceptable attaching means. As a result of the positioning of rod 35 between platform 11 and retainers 34 and the size of gaps 36 and 37, it is virtually impossible for rod 35 to slip out of retainer 34 during use.

Figure 4:
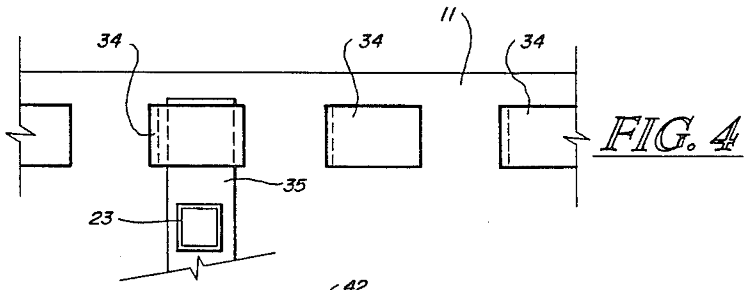
FIG. 4 is an expanded bottom view of the platform of the back traction table taken along lines 4—4 of FIG. 3 and showing in greater detail the construction of the means of balancing the platform of the back traction table.

FIG. 4 of the drawings shows the structure of retainers 34 and the positioning of leg 23 with respect to rod 35. Use of short sections of angle iron for retainers 34 ensures that retainers 34 and legs 23 and 24 do not interfere with one another. While only one set of retainers 34 on one side of platform 11 of back traction table 10 is here shown, such positioning and structure is typical, and a second set of such retainers 34 is positioned beneath and near the opposite side of platform 11 of back traction table 10.

Figure 5:
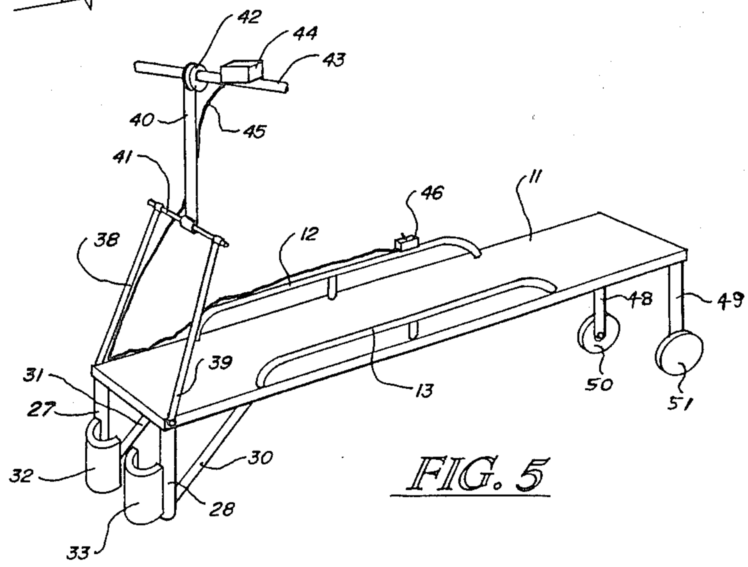
FIG. 5 is a perspective view showing an alternative embodiment of the back traction table of FIG. 1 illustrating how the platform and other parts of the back traction table of FIG. 1 may be utilized with a chain hoist for individuals having minimal physical capability.

FIG. 5 shows an alternative embodiment of the present invention. This alternative embodiment of back traction table 10 includes a platform 11 having side rails 12 and 13 provided to minimize the likelihood of an individual's rolling or falling off the side of platform 11. Legs 48 and 49, with wheels 50 and 51 respectively attached thereto, are attached to platform 11 at one end, and legs 28 and 27 are attached at the other end of platform 11. Leg supports 32 and 33 are provided to allow an individual to position his legs therein to minimize the likelihood of sliding on platform 11 during use of back traction table 10. Platform 11 is further attached to straps 38 and 39, which are in turn attached to a rod 41, which is attached to a structural piece 40. Structural piece 40 is flexible and can consist of a chain, strap or cable, and is attached to a pulley 42, which is attached to a rod 43 operated by a motor 44. Motor 44 can be operated by hydraulic, electric or any other means, but is controlled by means of control line 45 and control switch 46. Control switch 46 is positioned on hand rail 12 of platform 11 to facilitate use by an individual raising or lowering platform 11. As platform 11 is raised or lowered, back traction table 10 is free to move on wheels 50 and 51 in order to minimize stresses on the structure of back traction table 10. Such an alternative embodiment is provided for individuals who have minimal physical capability and are uncomfortable or incapable of dealing with the back traction table 10 of FIGS. 1 and 2.

While the foregoing description of the invention has shown preferred embodiments using specific terms, such description is presented for illustrative purposes only. It is applicant's intention that changes and variations may be made without departure from the spirit or scope of the following claims, and this disclosure is not intended to limit applicant's protection in any way.

I claim:

1. A back traction table, comprising:

a platform having a head end, a foot end, a top surface and a bottom surface;

a base having a top and a bottom;

balancing means positioned substantially at said top of said base;

a series of retainers attached to said bottom surface of said platform offset from each other and positioned at intervals between said foot end of said platform and said head end of said platform, attachable to said balancing means so that said platform substantially balances on said balancing means when positioned thereon, at least two of said retainers having a planar first portion oriented substantially perpendicular to said platform and planar second portion extending from the end of said first portion remote from said platform and oriented substantially perpendicular to said first portion and extending toward said head end of said platform, said retainers being sized and offset from each other so that said balancing means fits between said retainers and into an area between said second portion of one of said retainers and said bottom surface of said platform, thereby minimizing the likelihood that said platform will slip off of said balancing means during use of said back traction table, and a leg support positioned near said foot end of said platform which captures an individual's leg so that, when said individual lies down upon said top surface of said platform with said individual's head positioned toward said head end of said platform, said individual is restrained from sliding away from said foot end of said platform.

2. The invention of claim 1, including at least one hand rail attached to said platform positioned to restrain sideways movement of said individual.

3. The invention of claim 1, including a bumper means positioned between said platform and said base to limit the angle to which said platform tilts with respect to said base.

4. A back traction table, comprising:

a platform having a head end, a foot end, a top surface and a bottom surface;

a base having a top and a bottom;

balancing means positioned substantially at said top of said base;

attaching means attached to said bottom surface of said platform at a first point between said foot end of said platform and said head end of said platform, attachable to said balancing means so that said platform substantially balances on said balancing means when positioned thereon;

a leg support positioned near said foot end of said platform which captures an individual's leg so that, when said individual lies down upon said top surface of said platform with said individual's head positioned toward said head end of said platform, said individual is restrained from sliding away from said foot end of said platform, and a bumper means positioned between said platform and said base to limit the angle to which said platform tilts, consisting substantially of:

a structural support attached to said base, and a spring-loaded bumper contact positioned between said platform and said structural support so that, when said platform tilts and contacts said spring-loaded bumper contact, said spring-loaded bumper contact absorbs the impact, thereby minimizing jarring resulting therefrom.

5. The invention of claim 4, wherein said bumper means includes adjusting means for adjusting the position of said spring-loaded bumper contact with respect to said base.

* * * * *